United States Patent [19]
Bandman et al.

[11] Patent Number: 6,051,697
[45] Date of Patent: Apr. 18, 2000

[54] CHEMOKINE EXPRESSED IN EOSINOPHILS

[75] Inventors: Olga Bandman; Roger Coleman, both of Mountain View; Susan G. Stuart, Montara, all of Calif.

[73] Assignee: Incyte Pharmaceuticals, Inc., Palo Alto, Calif.

[21] Appl. No.: 09/113,705

[22] Filed: Jul. 10, 1998

Related U.S. Application Data

[62] Division of application No. 08/421,144, Apr. 13, 1995, Pat. No. 5,874,211.

[51] Int. Cl.$^7$ .......................... C07H 21/02; C07H 21/04; C12P 21/00
[52] U.S. Cl. ........................ 536/23.1; 536/22.1; 536/24.3; 536/24.31; 536/24.33; 536/24.5; 435/69.1
[58] Field of Search ..................... 435/69.1; 536/22.1, 536/23.1, 24.3, 24.31, 24.33, 24.5

[56] References Cited

U.S. PATENT DOCUMENTS

| | | | |
|---|---|---|---|
| 5,616,688 | 4/1997 | Cermai et al. | 530/351 |
| 5,703,046 | 12/1997 | Atkinson | 514/12 |

FOREIGN PATENT DOCUMENTS

WO94/11504  5/1994  WIPO .

OTHER PUBLICATIONS

Abu–Ghazaleh et al., *Immunol Ser.*, 57:137–167 (1992)—only abstracts available.

Capron, *Mem. Inst. Oswaldo Crus*, 87:83–89 (1992)—only abstracts available.

Guyton, *Textbook of Medical Physiology*, WB Saunders Co., Philadelphia, PA (1991), pp. 365–384.

Isselbacher, et al., *Harison's Principles of Internal Medicine*, McGraw–Hill, New York, NY (1994), pp. 1437–1504.

Zucker–Franklin, et al., Chapter 5, *Eosinophils, Atlas of Blood Cells, Function and Pathology*, Lea and Febiger, Philadelphia, PA (1988).

Schall, *Chemotactic Cytokines: Targets for Therapeutic Development*, International Busines Communications, Southborough, MA (1994) pp. 180–270.

Paul, *Fundamental Immunology*, Raven Press, New York, NY (1993) pp. 822–826.

Sommer, et al., "Minimal homology requirements for PCR primers", *Nucleic Acids Res.*, 17:6749, (1989).

Kwon, et al., "A new chemokine, MMRP2", GenBank Accession No. U15209, Sep. 1994.

*Primary Examiner*—Jeffrey Fredman
*Attorney, Agent, or Firm*—Incyte Pharmaceuticals, Inc.; Barbara J. Luther; Lynn E. Murry

[57] ABSTRACT

The present invention provides nucleotide and amino acid sequences that identify and encode a novel chemokine (EEC) expressed in human eosinophil cells. The present invention also provides for antisense molecules to the nucleotide sequences which encode EEC, expression vectors for the production of purified EEC, antibodies capable of binding specifically to EEC, hybridization probes or oligonucleotides for the detection of EEC-encoding nucleotide sequences, genetically engineered host cells for the expression of EEC, diagnostic tests for chemokine activation based on EEC-encoding nucleic acid molecules and antibodies capable of binding specifically to the protein.

7 Claims, 4 Drawing Sheets

```
5' ATG AAG GTC TCC GTG GCT GCC CTC TGC CTC ATG CTT GTT ACT GCC CTT GGA    54
   Met Lys Val Ser Val Ala Ala Leu Cys Leu Met Leu Val Thr Ala Leu Gly

TCC CAG GCC CGG GTC ACA AAA GAT GCA GAG ACA GAG TTC ATG ATG TCA AAG CTT  108
   Ser Gln Ala Arg Val Thr Lys Asp Ala Glu Thr Glu Phe Met Met Ser Lys Leu

CCA TTG GAA AAT CCA GTA CTT CTG GAC ATG CTC TGG AGG AGA AAG ATT GGT CCT  162
   Pro Leu Glu Asn Pro Val Leu Leu Asp Met Leu Trp Arg Arg Lys Ile Gly Pro

CAG ATG ACC CTT TCT CAT GCT GCA GGA TTC CAT GCT ACT AGT GCT GAC TGC TGC  216
   Gln Met Thr Leu Ser His Ala Ala Gly Phe His Ala Thr Ser Ala Asp Cys Cys

ATC TCC TAC ACC CCA CGA AGC ATC CCG TCA CTC CTG GAG CTC AGT TAC TTT GAA  270
   Ile Ser Tyr Thr Pro Arg Ser Ile Pro Ser Leu Leu Glu Leu Ser Tyr Phe Glu

ACG AAC AGC GAG TGC TCC AAG CCG GGT GTC ATC TTC CTC ACC AAG AAG GGG CGA  324
   Thr Asn Ser Glu Cys Ser Lys Pro Gly Val Ile Phe Leu Thr Lys Lys Gly Arg

CGT TTC TGT GCC AAC CCC AGT GAT AAG CAA GTT CAG GTT TGC ATG AGA ATG CTG  378
   Arg Phe Cys Ala Asn Pro Ser Asp Lys Gln Val Gln Val Cys Met Arg Met Leu

AAG CTG GAC ACA CGG ATC AAG ACC AGG AAG AAT 3'
   Lys Leu Asp Thr Arg Ile Lys Thr Arg Lys Asn
```

FIGURE 1

```
              M K V S V A A L S V L L L V A A L C - - - - - - - - - - - - - Majority
                        10              20              30
   1   M K V S V A A L S C L M L V T A L G S Q A R V T K D A E T E   New 288236
   1   M Q V S T A A L A V L L C T M A L C N Q - - - - - - - - - -   MIP-1a
   1   M K L C V T V L S L L M L V A A F C S P A - - - - - - - - -   MIP-1b
   1   M - - - - - - - - K V S A A - - - - - - - - - - - - - - - -   MCP-1
   1   - - - - - - - - - - - - - - - - - - - - - - - - - - - - - -   MCP-2
   1   M W K P M P S P S N M K A S A A - - - - - - - - - - - - - -   MCP-3
   1   M K V S A A R L A V I L I A T A L C A P A - - - - - - - - -   RANTES

- - - - - - - - D - - - - - - - - - - - - - - - - - - A Q Majority
                        40              50              60
  31   F M M S K L P L E N P V L L D M L W R R K I G P Q M T L S H   New 288236
  21   - F S A S L A A D T P - - - - - - - - - - - - - - - - - - -   MIP-1a
  22   - L S A P M G S D P P - - - - - - - - - - - - - - - - - - -   MIP-1b
   7   - - - - - - - - - - - L L C L L L I A A T F I P Q G L A Q     MCP-1
   1   - - - - - - - - - - - - - - - - - - - - - - - - - A Q         MCP-2
  17   - - - - - - - - - - - L L C L L L T A A A F S P Q G L A Q     MCP-3
  22   - S A S P Y S S D T - - - - - - - - - - - - - - - - - - - -   RANTES P - - - - - - - T T C C F S Y T N R K I P R Q R L E S Y F - Majority
                        70              80              90
  61   A A G F H A T S A D C C I S Y T P R S I P C S L L E S Y F -   New 288236
  31   - - - - - - - - - T A C C F S Y T S R Q I P Q N F I A D Y F - MIP-1a
  32   - - - - - - - - - T A C C F S Y T A R K L P R N F V V D Y Y - MIP-1b
  25   P D A I N - A P V T C C Y N F T N R K I S V Q R L A S Y R R   MCP-1
   3   P D S V S - I P I T C C F N V I N R K I P I Q R L E S Y T R   MCP-2
  35   P V G I N - T S T T C C Y R F I N K K I P K Q R L E S Y R R   MCP-3
  31   - - - - - - - - - T P C C F A Y I A R P L P R A H I K E Y F - RANTES E T S S Q C S K P A V I F K T K R G K E V C A D P S E K W V Majority
                        100             110             120
  90   E T N S E C S K P G V I F L T K G R R F C A N P S D K Q V   New 288236
  52   E T S S Q C S K P G V I F L T K R S R Q V C A D P S E E W V   MIP-1a
  53   E T S S L C S Q P A V V F Q T K R S K Q V C A D P S E S W V   MIP-1b
  54   I T S S K C P K E A V I F K T I V A K E I C A D P K Q K W V   MCP-1
  32   I T N I Q C P K E A V I F K T K R G K E V C A D P K E R W V   MCP-2
  64   T T S S H C P R E A V I F K T K L D K E I C A D P T Q K W V   MCP-3
  52   Y T S G K C S N P A V V F V T R K N R Q V C A N P E K K W V   RANTES Q D Y M K - L E L D K - - Q T - K -               Majority
                        130
 120   Q V C M R M L K L D T R I K T R K N                       New 288236
  82   Q K Y V S D L E L S A                                     MIP-1a
  83   Q E Y V Y D L E L N                                       MIP-1b
  84   Q D S M D - - H L D K Q T Q T P K T                       MCP-1
  62   R D S M K - - H L D Q I F Q N L K P                       MCP-2
  94   Q D F M K - - H L D K K T Q T P K L                       MCP-3
  82   R E Y I N S L E M S                                       RANTES
```

FIGURE 2

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 411 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: EOSINOPHILS
      (B) CLONE: 288236

(xi) SEQUENCE DESCRIPTION: SEQ ID NO:1:

```
ATGAAGGTCT CCGTGGCTGC CCTCTCCTGC CTCATGCTTG TTACTGCCCT TGGATCCCAG      60

GCCCGGGTCA CAAAAGATGC AGAGACAGAG TTCATGATGT CAAAGCTTCC ATTGGAAAAT     120

CCAGTACTTC TGGACATGCT CTGGAGGAGA AAGATTGGTC CTCAGATGAC CCTTTCTCAT     180

GCTGCAGGAT TCCATGCTAC TAGTGCTGAC TGCTGCATCT CCTACACCCC ACGAAGCATC     240

CCGTGTTCAC TCCTGGAGAG TTACTTTGAA ACGAACAGCG AGTGCTCCAA GCCGGGTGTC     300

ATCTTCCTCA CCAAGAAGGG GCGACGTTTC TGTGCCAACC CAGTGATAA GCAAGTTCAG      360

GTTTGCATGA GAATGCTGAA GCTGGACACA CGGATCAAGA CCAGGAAGAA T              411
```

(2) INFORMATION FOR SEQ ID NO:2:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (vii) IMMEDIATE SOURCE:
        (A) LIBRARY: Eosinophils
        (B) CLONE: 288236

(xi) SEQUENCE DESCRIPTION: SEQ ID NO:2:

```
Met Lys Val Ser Val Ala Ala Leu Ser Cys Leu Met Leu Val Thr Ala
 1               5                  10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Met Leu Trp
            35                  40                  45

Arg Arg Lys Ile Gly Pro Gln Met Thr Leu Ser His Ala Ala Gly Phe
 50                  55                  60

His Ala Thr Ser Ala Asp Cys Cys Ile Ser Tyr Thr Pro Arg Ser Ile
 65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
                100                 105                 110

Asn Pro Ser Asp Lys Gln Val Gln Val Cys Met Arg Met Leu Lys Leu
                115                 120                 125

Asp Thr Arg Ile Lys Thr Arg Lys Asn
                130                 135
```

(2) INFORMATION FOR SEQ ID NO:3:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
 50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                85                  90
```

(2) INFORMATION FOR SEQ ID NO:4:

(i) SEQUENCE CHARACTERISTICS:
        (A) LENGTH: 92 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:4:

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

(2) INFORMATION FOR SEQ ID NO:5:

(i) SEQUENCE CHARACTERISTICS:
            (A) LENGTH: 99 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr (2) INFORMATION FOR SEQ ID NO:6:

(i) SEQUENCE CHARACTERISTICS:
            (A) LENGTH: 77 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:6:

Ala Gln Pro Asp Ser Val Ser Ile Pro Ile Thr Cys Cys Phe Asn Val
1               5                   10                  15

Ile Asn Arg Lys Ile Pro Ile Gln Arg Leu Glu Ser Tyr Thr Arg Ile
                20                  25                  30

Thr Asn Ile Gln Cys Pro Lys Glu Ala Val Ile Phe Lys Thr Lys Arg

```
                    35                  40                  45
Gly Lys Glu Val Cys Ala Asp Pro Lys Glu Arg Trp Val Arg Asp Ser
    50                  55                  60
Met Lys His Leu Asp Gln Ile Phe Gln Asn Leu Lys Pro
 65                 70                  75
```

(2) INFORMATION FOR SEQ ID NO:7:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Trp Lys Pro Met Pro Ser Pro Ser Asn Met Lys Ala Ser Ala Ala
 1               5                  10                  15
Leu Leu Cys Leu Leu Leu Thr Ala Ala Ala Phe Ser Pro Gln Gly Leu
                20                  25                  30
Ala Gln Pro Val Gly Ile Asn Thr Ser Thr Thr Cys Cys Tyr Arg Phe
            35                  40                  45
Ile Asn Lys Lys Ile Pro Lys Gln Arg Leu Glu Ser Tyr Arg Arg Thr
    50                  55                  60
Thr Ser Ser His Cys Pro Arg Glu Ala Val Ile Phe Lys Thr Lys Leu
 65                 70                  75                  80
Asp Lys Glu Ile Cys Ala Asp Pro Thr Gln Lys Trp Val Gln Asp Phe
                85                  90                  95
Met Lys His Leu Asp Lys Lys Thr Gln Thr Pro Lys Leu
                100                 105
```

(2) INFORMATION FOR SEQ ID NO:8:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Lys Val Ser Ala Ala Arg Leu Ala Val Ile Leu Ile Ala Thr Ala
 1               5                  10                  15
Leu Cys Ala Pro Ala Ser Ala Ser Pro Tyr Ser Ser Asp Thr Thr Pro
                20                  25                  30
Cys Cys Phe Ala Tyr Ile Ala Arg Pro Leu Pro Arg Ala His Ile Lys
            35                  40                  45
Glu Tyr Phe Tyr Thr Ser Gly Lys Cys Ser Asn Pro Ala Val Val Phe
    50                  55                  60
Val Thr Arg Lys Asn Arg Gln Val Cys Ala Asn Pro Glu Lys Lys Trp
 65                 70                  75                  80
Val Arg Glu Tyr Ile Asn Ser Leu Glu Met Ser
                85                  90
```

(2) INFORMATION FOR SEQ ID NO:9:

(i) SEQUENCE CHARACTERISTICS:
        (A) LENGTH: 86 amino acids
        (B) TYPE: amino acid -continued

```
        (C) STRANDEDNESS: single
        (D) TOPOLOGY: linear (ii) MOLECULE TYPE: protein (xi) SEQUENCE DESCRIPTION: SEQ ID NO:9:

Met Lys Val Ser Val Ala Ala Leu Ser Val Leu Leu Val Ala Ala
1               5                   10                  15

Leu Cys Asp Ala Gln Pro Thr Thr Cys Cys Phe Ser Tyr Thr Asn Arg
                20                  25                  30

Lys Ile Pro Arg Gln Arg Leu Glu Ser Tyr Phe Glu Thr Ser Ser Gln
            35                  40                  45

Cys Ser Lys Pro Ala Val Ile Phe Lys Thr Lys Arg Gly Lys Glu Val
    50                  55                  60

Cys Ala Asp Pro Ser Glu Lys Trp Val Gln Asp Tyr Met Lys Leu Glu
65                  70                  75                  80

Leu Asp Lys Gln Thr Lys
                85
```

CHEMOKINE EXPRESSED IN EOSINOPHILS

This application is a divisional application of U.S. application Ser. No. 08/421,144, filed Apr. 13, 1995 now U.S. Pat. No. 5,874,211.

BACKGROUND OF THE INVENTION

Eosinophils are bi- or multi-nucleate white blood cells which contain basophilic or eosinophilic granules formed during their development by highly active golgi and ribosomal machinery. The plasma membrane is not structurally distinct from that of other leukocytes, but it is characterized by immunoglobulin (Ig) receptors, particularly IgG and IgE. These cells are formed throughout life from pluripotent stem cells and play a crucial role in systemic defense protecting the body from microorganisms and foreign proteins. In comparison to a total of 7000 white blood cells per microliter of blood, the number of eosinophils is normally about 160 cells per microliter. Eosinophils, generally six days worth, are formed and stored in the bone marrow until they are recruited to the site of inflammation or invasion.

Eosinophils have a special function in parasitic infections. They attach to parasitic larvae, presumably via their Ig receptors, and undergo degranulation in response to interleukin-5 (IL-5), IL-3, granulocyte/monocyte cell stimulating factor (GM-CSF) produced by activated T cells and mast cells of the host (Abu-Ghazaleh R I, Kita H, Gleich G J (1992) Immunol Ser 57:137–67) or other factors produced by the parasite. Degranulation releases many active species including the following: 1) hydrolytic enzymes such as peroxidase, acid phosphatase, phospholipase, B glucuronidase, ribonuclease, arylsulfatase and cathepsin; 2) highly reactive superoxides; and 3) major basic protein (MBP), an arginine-rich potent larvicidal polypeptide and eosinophil cationic protein (cf. Capron M (1992) Mem Inst Oswaldo Cruz 87(S5):83–9). Eosinophils are produced in great quantities in persons with helminthic infections such as hookworm, schistosomiasis, toxocariasis, trichuriasis, filariasis, strongyloidiasis, echinococcosis, cysticercosis, and trichinosis, etc.

Large numbers of eosinophils also collect in tissues such as the heart, lungs, central nervous system, sinuses and skin where allergic reactions commonly occur. They are chemoattracted to the site of inflammation or invasion by eosinophil chemotactic factor, platelet activation factor, complement 5a, or IL-5 which are released by mast cells and basophils during the allergic reaction. Eosinophils neutralize slow reacting substance of anaphylaxis (a mixture of leukotrienes) and histamine released by mast cells and basophils, produce eosinophil derived inhibitor which prevents degranulation of mast cells, and phagocytize antigen-antibody complexes—all of which downregulate the hypersensitivity response.

Eosinophilia, an excess of eosinophils—more than 500 per microliter of blood—is commonly observed in patients with allergies, hay fever, asthma and reactions to drugs as common as aspirin, sulfonamides and penicillins. Eosinophilia is also associated with rheumatoid arthritis and cancers such as Hodgkins lymphoma, chronic myelogenous leukemia, and carcinomas of the lung, stomach, pancreas, ovaries, uterus and liver. Eosinophilia may cause tissue damage by excessive degranulation and is usually treated with glucocorticoid chemotherapy.

Eosinophils, their morphology, function and relation to disease are reviewed, inter alia, in Guyton AC (1991) Textbook of Medical Physiology, W B Saunders Co, Philadelphia Pa.; Isselbacher K J et al (1994) Harrison's Principles of Internal Medicine, McGraw-Hill, New York City, pp. 1437–1504; and Zucker-Franklin D et al (1988) Atlas of Blood Cells, Function and Pathology, Lea and Febiger, Philadelphia Pa.

As is the case in inflammation of other tissues, leukocytes including monocytes, macrophages, basophils, and eosinophils infiltrate the inflamed area of the pancreas. Their primary role is to clean up the site of the inflammation; however, macrophages may produce powerful oxidants and proteases which contribute to tissue destruction. Leukocytes also secrete a range of cytokines which recruit other cells to the area.

The investigation of the critical, regulatory processes by which white cells proceed to their appropriate destination and interact with other cells is underway. The current model of leukocyte movement or trafficking from the blood to injured or inflamed tissues comprises the following steps. The first step is the rolling adhesion of the leukocyte along the endothelial cells of the blood vessel wall. This movement is mediated by transient interactions between selectins and their ligands. A second step involves cell activation which promotes a more stable leukocyte-endothelial cell interaction mediated by the integrins and their ligands. This stronger, more stable adhesion precipitates the final steps—leukocyte diapedesis and extravasation into the tissues.

The chemokine family of polypeptide cytokines possesses the cellular specificity required to explain leukocyte trafficking in different abnormal, inflammatory or diseased situations. First, chemokines mediate the expression of particular adhesion molecules on endothelial cells; and second, they generate gradients of chemoattractant factors which activate specific cell types. In addition, the chemokines stimulate the proliferation of specific cell types and regulate the activation of cells which bear specific receptors. These activities demonstrate a high degree of target cell specificity.

The chemokines are small polypeptides, generally about 70–100 amino acids (aa) in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four-cysteine motif which is based primarily on the spacing of the first two cysteine residues in the mature molecule. Currently the chemokines are assigned to one of two families, the C—C chemokines ($\alpha$) and the C—X—C chemokines ($\beta$). Although exceptions exist, the C—X—C chemokines generally activate neutrophils and fibroblasts while the C—C chemokines act on a more diverse group of target cells which include monocytes/macrophages, basophils, eosinophils, T lymphocytes and others. The known chemokines of both families are synthesized by many diverse cell types as reviewed in Thomson A. (1994) The Cytokine Handbook, 2d Ed. Academic Press, NY. The two groups of chemokines will be described in turn.

At this time, relatively few C—C chemokines have been described, and they appear to have less N-terminal processing than the C—X—C chemokines. A brief description of the known human (and/or murine) C—C chemokines follows. The macrophage inflammatory proteins alpha and beta (MIP-1$\alpha$ and $\beta$) were first purified from stimulated mouse macrophage cell line and elicited an inflammatory response when injected into normal tissues. At least three distinct and non-allelic genes encode human MIP-1α and seven distinct genes encode MIP-1β.

MIP-1α and MIP-1β consist of 68–69 aa which are about 70% identical in their acidic, mature secreted forms. They are both expressed in stimulated T cells, B cells and monocytes in response to mitogens, anti-CD3 and endotoxin, and both polypeptides bind heparin. While both molecules stimulate monocytes, MIP-1α chemoattracts the CD-8 subset of T lymphocytes and eosinophils, while MIP-1β chemoattracts the CD-4 subset of T lymphocytes. In mouse, these proteins are known to stimulate myelopoiesis.

I-309 was cloned from a human γ-δT cell line and shows 42% aa identity to T cell activation gene 3 (TCA3) cloned from mouse. There is considerable nucleotide homology between the 5' flanking regions of these two proteins, and they share an extra pair of cysteine residues not found in other chemokines. Such similarities suggest I-309 and TCA3 are species homologs which have diverged over time in both sequence and function.

RANTES is another C—C chemokine which is expressed in T cells (but not B cells), in platelets, in some tumor cell lines, and in rheumatoid synovial fibroblasts. In the latter, it is regulated by interleukins-1 and -4, transforming nerve factor and interferon-γ. The cDNA cloned from T cells encodes a basic 8 kD protein which lacks N-linked glycosylation and is able to affect lymphocytes, monocytes, basophils and eosinophils. The expression of RANTES mRNA is substantially reduced following T cell stimulation.

Monocyte chemotactic protein (MCP-1) is a 76 aa protein which appears to be expressed in almost all cells and tissues upon stimulation by a variety of agents. The targets of MCP-1, however, are limited to monocytes and basophils in which it induces a MCP-1 receptor:G protein-linked calcium flux (Charo I, personal communication). Two other related proteins (MCP-2 and MCP-3) were purified from a human osteosarcoma cell line. MCP-2 and MCP-3 have 62% and 73% aa identity, respectively, with MCP-1 and share its chemoattractant specificity for monocytes.

Current techniques for diagnosis of abnormalities in the inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of newdiagnostic techniques comprising small molecules such as the expressed chemokines are important to provide for early and accurate diagnoses, to give a better understanding of pathology at the molecular level. Current methods of treating eosinophil-related conditions involve administration of steroids and other drugs with multiple side effects. A new chemokine can be used to develop more specific drugs with fewer side effects.

The chemokine molecules are reviewed in Schall T J (1994) Chemotactic Cytokines: Targets for Therapeutic Development. International Business Communications, Southborough Mass., pp 180–270; and in Paul W E (1993) Fundamental Immunology, Raven Press, New York City, pp 822–826.

SUMMARY OF THE INVENTION

The subject invention provides a unique nucleotide sequence which encodes a novel eosinophilic protein. The new gene, which is known as eosinophilic expressed chemokine, or eec (Incyte Clone 288236), encodes the polypeptide designated EEC, a new member of the C—C chemokine family.

The invention also comprises diagnostic tests for physiologic or pathologic activity of eosinophils which include the steps of testing a sample or an extract thereof with eec DNA, fragments or oligomers thereof. Further aspects of the invention include the antisense DNA of eec; cloning or expression vectors containing eec; host cells or organisms transformed with expression vectors containing eec; a method for the production and recovery of purified EEC from host cells; purified protein, EEC; antibodies to EEC, and diagnostic tests for eosinophilia.

DESCRIPTION OF THE FIGURES

FIG. 1 displays the nucleotide sequence for eec and the predicted amino acid sequence of the eosinophilic expressed chemokine, EEC.

FIG. 2 shows the amino acid alignment of EEC with other human chemokines of the C—C family including MIP-1a, SEQ ID NO:3; MIP-1b, SEQ ID NO:4; MCP-1, SEQ ID NO:5; MCP-2, SEQ ID NO:6; MCP-3, SEQ ID NO:7; RANTES, SEQ ID NO:8; and Majority, SEQ ID NO:9. Alignments shown were produced using the multisequence alignment program of LASERGENE software (DNASTAR Inc, Madison Wis.).

DETAILED DESCRIPTION OF THE INVENTION

Definitions

Figure 3:
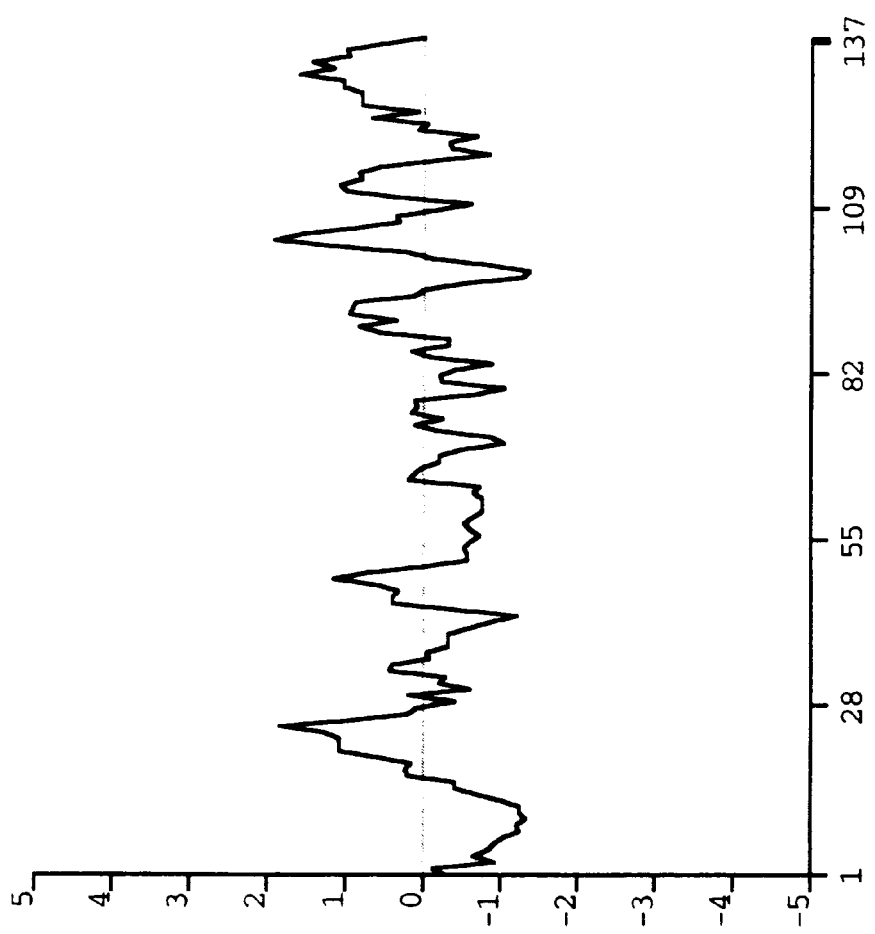
FIG. 3 displays an analysis of EEC hydrophobicity based on the predicted amino acid sequence and composition.

As used herein, "eosinophil expressed chemokine" or EEC, refers to a polypeptide, naturally occurring EEC or active fragments thereof, which are encoded by mRNAs transcribed from the cDNA of SEQ ID NO:1.

"Active" refers to those forms of EEC which retain biologic and/or immunologic activities of any naturally occurring EEC.

"Naturally occurring EEC" refers to EEC produced by human cells that have not been genetically engineered and specifically contemplates various EECs arising from post-translational modifications of the polypeptide including but not limited to acetylation, carboxylation, glycosylation, phosphorylation, lipidation and acylation.

"Derivative" refers to polypeptides derived from naturally occurring EEC by chemical modifications such as ubiquitination, labeling (e.g., with radionuclides, various enzymes, etc.), pegylation (derivatization with polyethylene glycol), or by insertion or substitution by chemical synthesis of aa such as ornithine, which do not normally occur in human proteins.

"Recombinant variant" refers to any polypeptide differing from naturally occurring EEC by aa insertions, deletions, and substitutions, created using recombinant DNA techniques. Guidance in determining which aa residues may be replaced, added or deleted without abolishing activities of interest, such as cell adhesion and chemotaxis, may be found by comparing the sequence of the particular EEC with that of homologous cytokines and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in an EEC molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment"0 is a stretch of aa residues of at least about 5 amino acids, often at least about 7 aa, typically at least about 9 to 13 aa, and, in various embodiments, at least about 17 or more aa. To be active, any EEC polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

Eosinophilia is defined as a dramatic increase in the number of eosinophils per microliter of blood. It has been observed in the following: 1) collagen vascular diseases such as rheumatoid arthritis, eosinophilic fasciitis, allergic angitis, periarteritis nodosa, and granulomatosis; 2) malignancies such as Hodgkin's lymphoma, mycosis fungoides, chronic myelogenous leukemia and cancer of the lung, stomach, pancreas, ovaries or uterus; 3) helminthic infections such as hookworm, schistosomiasis, toxocariasis, trichuriasis, filariasis, strongyloidiasis, echinococcosis, cysticercosis, and trichinosis, 4) hypereosinophilic syndromes such as Loeffler's syndrome, Loeffler's endocarditis, eosinophilic leukemia, eosinophil myalgia, and idiopathic hypereosinophilic syndrome; and 5) allergies and asthma.

The present invention includes purified EEC polypeptides from natural or recombinant sources, cells transformed with recombinant nucleic acid molecules encoding EEC. Various methods for the isolation of the EEC polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol 182, Academic Press, San Diego Calif.; and Scopes R (1982) Protein Purification: Principles and Practice. Springer-Verlag, New York City, both incorporated herein by reference.

"Recombinant" may also refer to a polynucleotide which encodes EEC and is prepared using recombinant DNA techniques. The DNAs which encode EEC may also include allelic or recombinant variants and mutants thereof.

"Oligonucleotides" or "nucleic acid probes" are prepared based on the cDNA sequences which encode EEC provided by the present invention. Oligonucleotides comprise portions of the DNA sequence having at least about 15 nucleotides, usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs encoding EEC are present in a cell or tissue or to isolate similar nucleic acid sequences from chromosomal DNA as described by Walsh P S et al (1992, PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to ligand-binding affinities, interchain affinities, or polypeptide degradation or turnover rate. One example involves inserting a stop codon into the nucleotide sequence to limit the size of EEC so as to provide a smaller, binding, non-activating ligand which would serve to block the activity of the natural chemokine.

Detailed Description of the Invention

The present invention provides a nucleotide sequence uniquely identifying a novel chemokine of the C—C family, EEC, which is highly expressed in the eosinophil. Because EEC is specifically expressed in eosinophil, the nucleic acids (eec), polypeptides (EEC) and antibodies to EEC are useful in diagnostic assays based on chemokine production in cases of inflammation or disease affecting the number and function of eosinophils. Excessive expression of EEC can also activate monocytes, macrophages, basophils, T lymphocytes and/or other cells which respond to the chemokines and result in the production of abundant proteases and other molecules which can lead to tissue damage or destruction. Therefore, a diagnostic test for excess expression of EEC can accelerate diagnosis and proper treatment of eosinophilia an abnormal condition caused by viral, bacterial, fungal or parasitic infections; mechanical injury associated with trauma; hereditary diseases such as allergies and asthma; infiltrative diseases such as leukemias and lymphomas; or other physiologic and pathologic problems associated with changes in the numbers of eosinophils.

The nucleotide sequences encoding EEC (or their complement) have numerous applications in techniques known to those skilled in the art of molecular biology. These techniques include use as hybridization probes, use in the construction of oligomers for PCR, use for chromosome and gene mapping, use in the recombinant production of EEC, and use in generation of anti-sense DNA or RNA, their chemical analogs and the like. Uses of nucleotides encoding EEC disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of EEC-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring eec, and all such variations are to be considered as being specifically disclosed.

Although the nucleotide sequences which encode EEC and/or its variants are preferably capable of hybridizing to the nucleotide sequence of the naturally occurring eec under stringent conditions, it may be advantageous to produce nucleotide sequences encoding EEC or its derivatives possessing a substantially different codon usage. Condons can be selected to increase the rate at which expression of the peptide occurs in a particular prokaryotic or eukaryotic expression host in accordance with the frequency with which particular codons are utilized by the host. Other reasons for substantially altering the nucleotide sequence encoding EEC and/or its derivatives without altering the encoded aa sequence include the production of RNA transcripts having more desirable properties, such as a greater half-life, than transcripts produced from the naturally occurring sequence.

Nucleotide sequences encoding EEC may be joined to a variety of other nucleotide sequences by means of well established recombinant DNA techniques (cf Sambrook J et al. supra). Useful nucleotide sequences for joining to eec include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for eec-specific nucleic acid hybridization probes capable of hybridizing with naturally occurring nucleotide sequences encoding EEC. Such probes may also be used for the detection of similar chemokine encoding sequences and should preferably contain at least 50% of the nucleotides from a C—C encoding sequence. The hybridization probes of the subject invention may be derived from the nucleotide sequences of the SEQ ID NO:1 or from genomic sequences including promoters, enhancer elements and/or possible introns of the respective naturally occurring eecs. Hybridization probes may be labeled by a variety of reporter groups, including radionuclides such as 32P or 35S, enzymatic labels such as alkaline phosphatase coupled to the probe via avidin/biotin coupling systems, and the like.

PCR as described U.S. Pat. Nos. 4,683,195; 4,800,195; and 4,965,188 provides additional uses for oligonucleotides based upon the nucleotide sequence which encodes EEC. Such probes used in PCR may be of recombinant origin, may be chemically synthesized, or a mixture of both, and comprise a discrete nucleotide sequence for diagnostic use or a degenerate pool of possible sequences for identification of closely related genomic sequences.

Other means of producing specific hybridization probes for eec DNAs include the cloning of nucleic acid sequences encoding EEC or EEC derivatives into vectors for the production of mRNA probes. Such vectors are known in the art, and are commercially available and may be used to synthesize RNA probes in vitro by means of the addition of the appropriate RNA polymerase such as T7 or SP6 RNA polymerase and the appropriate radioactively labeled nucleotides.

It is now possible to produce a DNA sequence, or portions thereof, encoding EEC and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the eec sequences or any portion thereof.

The nucleotide sequence can be used in an assay to detect inflammation or disease associated with abnormal levels of expression of EEC. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for eec can be used to construct hybridization probes for mapping that gene. The nucleotide sequence provided herein may be mapped to a particular chromosome or to specific regions of that chromosome using well known genetic and/or chromosomal mapping techniques. These techniques include in situ hybridization, linkage analysis against known chromosomal markers, hybridization screening with libraries, flow-sorted chromosomal preparations, or artificial chromosome constructions YAC or P1 constructions. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of eec on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding EEC may be used to produce purified EEC using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. EEC may be expressed in a variety of host cells, either prokaryotic or eukaryotic. Host cells may be from the same species in which eec nucleotide sequences are endogenous or from a different species. Advantages of producing EEC by recombinant DNA technology include obtaining adequate amounts of the protein for purification and the availability of simplified purification procedures.

Cells transformed with DNA encoding EEC may be cultured under conditions suitable for the expression of chemokines and recovery of the protein from the cell culture. EEC produced by a recombinant cell may be secreted or may be contained intracellularly, depending on the particular genetic construction used. In general, it is more convenient to prepare recombinant proteins in secreted form. Purification steps vary with the production process and the particular protein produced.

In addition to recombinant production, fragments of EEC may be produced by direct peptide synthesis using solid-phase techniques (cf Stewart et al (1969) Solid-Phase Peptide Synthesis, WH Freeman Co, San Francisco Calif.; Merrifield J (1963) J Am Chem Soc 85:2149–2154). In vitro protein synthesis may be performed using manual techniques or by automation. Automated synthesis may be achieved, for example, using Applied Biosystems 431A Peptide synthesizer (PE Biosystems, Foster City, Calif.) in accordance with the instructions provided by the manufacturer. Various fragments of EEC may be chemically synthesized separately and combined using chemical methods to produce the full length molecule.

EEC for antibody induction does not require biological activity; however, the protein must be immunogenic. Peptides used to induce specific antibodies may have an aa sequence consisting of at least five aa, preferably at least 10 aa. They should mimic a portion of the aa sequence of the protein and may contain the entire aa sequence of a small naturally occurring molecule such as EEC. Short stretches of EEC aa may be fused with those of another protein such as keyhole limpet hemocyanin and the chimeric molecule used for antibody production.

Antibodies specific for EEC may be produced by inoculation of an appropriate animal with the polypeptide or an antigenic fragment. An antibody is specific for EEC if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837; or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding EECs.

An additional embodiment of the subject invention is the use of EEC specific antibodies, inhibitors, receptors or their analogs as bioactive agents to treat eosinophilia, inflammation or disease involving an altered number of eosinophils including, but not limited to viral, bacterial, fungal or parasitic infections; mechanical injury associated with trauma; hereditary diseases such as allergies and asthma; infiltrative diseases such as leukemias and lymphomas; or other physiologic and pathologic problems associated with changes in the numbers of eosinophils.

Bioactive compositions comprising agonists, antagonists, receptors or inhibitors of EEC may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving eosinophil production and function.

The examples below are provided to illustrate the subject invention. These examples are provided by way of illustration and are not included for the purpose of limiting the invention.

EXAMPLES

I Isolation of mRNA and Construction of cDNA Libraries

The eec sequence was identified among the sequences comprising the human eosinophil library. The eosinophils used for this library were obtained via aphoresis of a 56 year old Caucasian male patient at Mayo Clinic (Rochester Minn.) who had been diagnosed with hypereosinophilic syndrome. The cells were washed twice in phosphate buffered saline and lysed immediately in a buffer containing guanidinium isothiocyanate. The lysate was centrifuged over a CsCl cushion, ethanol precipitated, resuspended in water and treated with DNase for 15 min at 37° C. The RNA was extracted with phenol chloroform and precipitated with ethanol. Polyadenylated messages were isolated using OLIGOTEX (Qiagen Inc, Chatsworth Calif.), and the cDNA library was constructed by Stratagene (11011 North Torrey Pines Road, La Jolla Calif. 92037).

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme, extracted with phenol chloroform, and fractionated by size on SEPHACRYL S4000 resin (Amersham Pharmacia Biotech (Piscataway N.J.). DNA of the appropriate size was then ligated to dephosphorylated LAMBDAZAP® arms (Stratagene) and packaged using GIGAPACK extracts (Stratagene). PBLUESCRIPT (Stratagene) phagemid DNAs were excised en masse from the eosinophil library and individual plasmid DNAs were made using MINIPREP Kits supplied by Advanced Genetic Technologies Corporation (Gaithersburg Md.).

These kits provide a 96-well format and enough reagents for 960 purifications. The recommended protocol supplied with each kit has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 $\mu$l of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block (Beckman Coulter, Fulton Calif.) for storage.

The quality of the cDNA library was determined by performing a pilot scale analysis of 192 cDNAs and checking for percentages of clones containing vector alone, mitochondrial or repetitive DNA sequences and clones originating from lambda or E. coli DNA. The numbers of exact/homologous matches to public databases, as well as the number of unique sequences—those having no known match in any available database—were also recorded.

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the PBLUESCRIPT plasmid and the cDNA insert. The phagemid DNA was released from the cells and purified, then used to re-infect fresh bacterial host cells (SOLR, Stratagene Inc), where the double-stranded phagemid DNA was produced. Because the phagemid carries the gene for B-lactamase, the newly transformed bacteria were selected on medium containing ampicillin.

Phagemid DNA was purified using the QIAWELL-8 Plasmid Purification System from QIAGEN®. This technique provides a rapid and reliable high-throughput method for lysing the bacterial cells and isolating highly purified phagemid DNA. The DNA eluted from the purification resin was suitable for DNA sequencing and other analytical manipulations.

II Sequencing of cDNA Clones

The cDNA inserts from random isolates of the human eosinophil library were sequenced in part. Methods for DNA sequencing are well known in the art. Conventional enzymatic methods employed DNA polymerase Klenow fragment, SEQUENASE (Amersham Pharmacia Biotech) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the ABI PRISM 377 or 373 DNA sequencing systems (PE Biosystems).

III Homology Searching of cDNA Clones and Deduced Proteins

Each sequence so obtained was compared to sequences in GenBank using a search algorithm developed by Applied Biosystems Inc. and incorporated into the INHERT™ 670 Sequence Analysis system. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 Sequence Analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

The nucleotide and amino acid sequences for the entire coding region of the eosinophil expressed chemokine, EEC, claimed in this invention are shown in FIG. 1.

IV Identification and Full Length Sequencing of the Genes

From all of the randomly picked and sequenced clones of the human eosinophil library, the eec sequence was homologous to but clearly different from any known C—C chemokine molecule. The complete nucleotide sequence for eec was translated, and the inframe translation is shown in FIG. 1. When all three possible predicted translations of the sequence were searched against protein databases such as SwissProt and PIR, no exact matches were found to the possible translations of eec. FIG. 2 shows the comparison of the EEC amino acid sequence with those of other C—C chemokine molecules. The substantial regions of homology among these molecules which includes the definitive C—C motif are shaded. Hydrophobicity plots for EEC are shown as FIG. 3. The phylogenetic analysis (FIG. 4) shows how closely eec is related to other well characterized human C—C chemokines. The most related of these molecules cluster together at the right hand side of the figure.

V Antisense analysis

Knowledge of the correct, complete cDNA sequence of the novel expressed chemokine gene will enable its use in antisense technology in the investigation of gene function. Oligonucleotides, genomic or cDNA fragments comprising the antisense strand of eec can be used either in vitro or in vivo to inhibit expression of the protein. Such technology is now well known in the art, and probes can be designed at various locations along the nucleotide sequence. By treatment of cells or whole test animals with such antisense sequences, the gene of interest can effectively be turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VI Expression of EEC

Expression of eec may be accomplished by subcloning the cDNAs into appropriate expression vectors and transfecting the vectors into appropriate expression hosts. In this particular case, the cloning vector previously used for the generation of the tissue library also provide for direct expression of the included eec sequence in *E coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The eec cDNA can be shuttled into other vectors known to be useful for expression of protein in specific hosts.

Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or 7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced EEC can be recovered from the conditioned medium and analyzed using chromatographic methods known in the art.

VII Isolation of Recombinant EEC

EEC may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the eec sequence may be useful to facilitate expression of EEC.

VIII Production of EEC Specific Antibodies

Two approaches are utilized to raise antibodies to EEC, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

Figure 4:
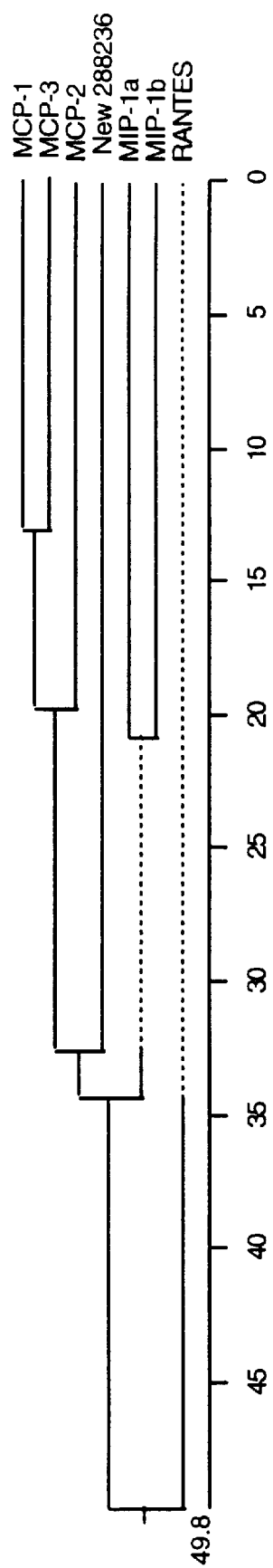
FIG. 4 shows a relatedness tree of human C—C chemokines. The phylogenetic tree was generated by phylogenetic tree program of LASERGENE software (DNASTAR) using the Clustal method with the PAM250 residue weight table.

In the second approach, the amino acid sequence of EEC, as deduced from translation of the cDNA, is analyzed to determine regions of high immunogenicity. Oligopeptides comprising appropriate hydrophilic regions, as shown in FIG. 3, are synthesized and used insuitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma-Aldrich, St. Louis Mo.) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled EEC to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/mi. The coated wells are blocked with 1% BSA, washed and exposed to supernatants from hybridomas. After incubation the wells are exposed to labeled EEC, 1 mg/ml. Clones producing antibodies will bind a quantity of labeled EEC which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual. Cold Spring Harbor Laboratory, Cold Spring Harbor N.Y.; and in Goding (1986) Monoclonal Antibodies: Principles and Practice, Academic Press, New York City, both incorporated herein by reference.

IX Diagnostic Test Using EEC Specific Antibodies

Particular EEC antibodies are useful for the diagnosis of prepathologic conditions, and chronic or acute diseases which are characterized by differences in the amount or distribution of EEC. To date, EEC has only been found in the human eosinophil library and is thus specific for abnormalities or pathologies which affect the eosinophil.

Diagnostic tests for EEC include methods utilizing the antibody and a label to detect EEC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound EEC, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EEC is preferred, but a competitive binding assay may be employed. These assays are described, among other places, in Maddox, DE et al (1983, J Exp Med 158:1211).

X Purification of Native EEC Using Specific Antibodies

Native or recombinant EEC can be purified by immunoaffinity chromatography using antibodies specific for EEC. In general, an immunoaffinity column is constructed by covalently coupling the anti-EEC antibody to an activated chromatographic resin.

Polyclonal immunoglobulins are prepared from immune sera either by precipitation with ammonium sulfate or by purification on immobilized Protein A (Amersham Pharmacia Biotechnology). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE (Amersham Pharmacia Biotechnology). The antibody is coupled to the resin, the resin is blocked, and the derivative resin is washed according to the manufacturer's instructions.

Such immunoaffinity columns are utilized in the purification of EEC by preparing a fraction from cells containing EEC in a soluble form. This preparation is derived by solubilization of the whole cell or of a subcellular fraction obtained via differential centrifugation by the addition of detergent or by other methods well known in the art. Alternatively, soluble EEC containing a signal sequence may be secreted in useful quantity into the medium in which the cells are grown.

A soluble EEC-containing preparation is passed over the immunoaffinity column, and the column is washed under conditions that allow the preferential absorbance of chemokines((eg, high ionic strength buffers in the presence of detergent). Then, the column is eluted under conditions that disrupt antibody/chemokine binding (e.g., a buffer of pH 2–3 or a high concentration of a chaotrope such as urea or thiocyanate ion), and EEC is collected.

XI EEC Induced Chemotaxis or Cell Activation

The chemotactic activity of EEC is measured in 48-well microchemotaxis chambers (Falk W R et al (1980) J Immunol Methods 33:239). In each well, two compartments are separated by a filter that allows the passage of cells in response to a chemical gradient. Cell culture medium such as RPMI 1640 (Sigma, St. Louis Mo.) containing the expressed chemokine is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing the chemokine are typed and quantified.

The specificity of the chemoattraction is determined by performing the chemotaxis assay on specific populations of cells. First, blood cells obtained from venipuncture are fractionated by density gradient centrifugation and the chemotactic activity of EEC is tested on enriched populations of neutrophils, peripheral blood mononuclear cells, monocytes and lymphocytes. Optionally, such enriched cell populations are further fractionated using CD8+ and CD4+ specific antibodies for negative selection of CD4+ and CD8+ enriched T-cell populations, respectively.

Another assay elucidates the chemotactic effect of EEC on activated T-cells. There, unfractionated T-cells or fractionated T-cell subsets are cultured for 6 to 8 hours in tissue culture vessels coated with CD-3 antibody. After this CD-3 activation, the chemotactic activity of EEC is tested as described above. Many other methods for obtaining enriched cell populations are known in the art.

Some chemokines also produce a non-chemotactic cell activation of neutrophils and monocytes. This is tested via standard measures of neutrophil activation such as actin polymerization, increase in respiratory burst activity, degranulation of the azurophilic granule and mobilization of $Ca^{++}$ as part of the signal transduction pathway. The assay for mobilization of $Ca^{++}$ involves preloading neutrophils with a fluorescent probe whose emission characteristics have been altered by $Ca^{++}$ binding. When the cells are exposed to an activating stimulus, $Ca^{++}$ flux is determined by observation of the cells in a fluorometer. The measurement of $Ca^{++}$ mobilization has been described in Grynkievicz G et al (1985) J Biol Chem 260:3440, and McColl S et al (1993) J Immunol 150:4550–4555, incorporated herein by reference.

Degranulation and respiratory burst responses are also measured in monocytes (Zachariae COC et al. (1990) J Exp Med 171: 2177–82). Further measures of monocyte activation are regulation of adhesion molecule expression and cytokine production (Jiang Y et al (1992) J Immunol 148: 2423–8). Expression of adhesion molecules also varies with lymphocyte activation (Taub D et al (1993) Science 260: 355–358).

XII Drug Screening

This invention is particularly useful for screening compounds by using EEC polypeptide or binding fragments thereof in any of a variety of drug screening techniques. The chemokine polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between EEC and the agent being tested. Alternatively, one can examine the diminution in complex formation between EEC and its target cell, monocyte, etc. caused by the agent being tested.

Thus, the present invention provides methods of screening for drugs or any other agents which can affect inflammation and disease. These methods comprise contacting such an agent with a EEC polypeptide or fragment thereof and assaying (i) for the presence of a complex between the agent and the EEC polypeptide or fragment, or (ii) for the presence of a complex between the EEC polypeptide or fragment and the cell, by methods well known in the art. In such competitive binding assays, the chemokine polypeptide or fragment is typically labeled. After suitable incubation, free EEC polypeptide or fragment is separated from that present in bound form, and the amount of free or uncomplexed label is a measure of the ability of the particular agent to bind to EEC or to interfere with the EEC and agent complex.

Another technique for drug screening provides high throughput screening for compounds having suitable binding affinity to the EEC polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with EEC polypeptide and washed. Bound EEC polypeptide is then detected by methods well known in the art. Purified EEC can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding EEC specifically compete with a test compound for binding to chemokine polypeptides or fragments thereof. In this manner, the antibodies can be used to detect the presence of any peptide which shares one or more antigenic determinants with EEC.

XIII Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous chemokine-like molecules or to identify efficient inhibitors. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the EEC amino acid sequence provided herein will provide guidance to those employing computer modeling techniques in place of or in addition to x-ray crystallography.

XIV Identification of EEC Receptors

Purified EEC are useful for characterization and purification of specific cell surface receptors and other binding molecules. Cells which respond to EEC by chemotaxis or other specific responses are likely to express a receptor for EEC. Radioactive labels may be incorporated into EEC by various methods known in the art. A preferred embodiment is the labeling of primary amino groups in EEC with 125I Bolton-Hunter reagent (Bolton, A E and Hunter, W M (1973) Biochem J 133: 529), which has been used to label other chemokines without concomitant loss of biological activity (Hebert C A et al (1991) J Biol Chem 266: 18989; McColl S et al (1993) J Immunol 150:4550–4555). Receptor-bearing cells are incubated with the labeled chemokine molecule. The cells are then washed to removed unbound chemokine, and receptor-bound labeled molecule is quantified. The data obtained using different concentrations of EEC are used to calculate values for the number and affinity of receptors.

Labeled EEC is also useful as a reagent for purification of its specific receptor. In one embodiment of affinity purification, the chemokine is covalently coupled to a chromatography column. Receptor-bearing cells are extracted, and the extract is passed over the column. The receptor binds to the column by virtue of its biological affinity for EEC. The receptor is recovered from the column and subjected to N-terminal protein sequencing. This amino acid sequence is then used to design degenerate oligonucleotide probes for cloning the receptor gene.

In an alternate method, mRNA is obtained from receptor-bearing cells and made into a cDNA library. The library is transfected into a population of cells, and those cells expressing the receptor are selected using fluorescently labeled EEC. The EEC specific receptor is identified by recovering and sequencing recombinant DNA from highly labeled cells.

In another alternate method, antibodies are raised against the surface of receptor-bearing cells, specifically monoclonal antibodies. The monoclonal antibodies are screened to identify those which inhibit the binding of labeled EEC. These monoclonal antibodies are then used in affinity purification or expression cloning of the receptor.

Soluble receptors or other soluble binding molecules are identified in a similar manner. Labeled EEC is incubated with extracts or other appropriate materials derived from the eosinophil. After incubation, EEC complexes (which are larger than the size of the purified chemokine molecule) are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or for cloning, if the soluble protein is unknown.

XV Use and Administration of EEC

Antibodies, inhibitors, receptors or antagonists of EEC (or other treatments for excessive chemokine production, hereinafter abbreviated TEC), can provide different effects when administered therapeutically. TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, receptor or antagonist being formulated and the condition to be treated. Characteristics of TEC include solubility of the molecule, half-life and antigenicity/immuno-genicity; these and other characteristics may aid in defining an effective carrier. Native human proteins are preferred as TECs, but organic or synthetic molecules resulting from drug screens may be equally effective in particular situations.

TECs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or U.S. Pat. No. 5,225,212. It is anticipated that different formulations will be effective for different TECs and that administration targeting the eosinophil may necessitate delivery in a manner different from that to another organ or tissue.

It is contemplated that conditions or diseases of the eosinophil which activate monocytes, macrophages, basophils, eosinophils or other leukocytes may precipitate damage that is treatable with TECs. Eosinophilia may be specifically diagnosed by the tests discussed above, and such testing should be performed in suspected cases of viral, bacterial, fungal or parasitic infections as recited herein; mechanical injuries associated with trauma; hereditary diseases such as allergies, asthma, and rheumatoid arthritis; cancers such as the recited carcinomas, leukemias, and lymphomas; or other physiologic or pathologic problems associated with changes in the numbers of eosinophils.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

We claim:

1. An isolated and purified polynucleotide capable of expressing eosinophil expressed chemokine, which comprises SEQ ID NO 1.

2. The polynucleotide of claim 1 further comprising control sequences for overexpression.

3. The polynucleotide of claim 1 comprising a recombinant DNA molecule whose nucleotide sequence is shown in SEQ ID NO 1.

4. The antisense DNA of the DNA molecule of claim 1.

5. An expression vector comprising the DNA molecule of claim 1.

6. A host cell transformed with the expression vector of claim 5.

7. A method for producing the eosinophil expressed chemokine polypeptide (EEC), said method comprising the steps of a) culturing the host cells of claim 6 under conditions suitable for the expression of EEC; and b) recovering EEC from the cell culture.

* * * * *